United States Patent [19]
Motoyuki et al.

[11] Patent Number: 6,011,190
[45] Date of Patent: *Jan. 4, 2000

[54] PROCESS FOR PREPARING DIALKYLNAPHTHALENE

[75] Inventors: Masahiro Motoyuki, Osaka; Koji Yamamoto, Kobe, both of Japan; Ajit Vishwanath Sapre; John Paul McWilliams, both of Paulsboro, N.J.

[73] Assignees: Kabushiki Kaisha Kobe Seiko Sho, Kobe, Japan; Mobil Oil Corporation, Fairfax, Va.

[*] Notice: This patent is subject to a terminal disclaimer.

[21] Appl. No.: 08/887,052

[22] Filed: Jul. 2, 1997

[51] Int. Cl.[7] .............................. C07C 1/01; C07C 2/64; C07C 2/68; C07C 5/22
[52] U.S. Cl. .................... 585/323; 585/313; 585/449; 585/467; 585/475; 585/481; 585/320
[58] Field of Search ................................ 585/313, 323, 585/444, 467, 475, 481, 320

[56] References Cited

U.S. PATENT DOCUMENTS

| | | | |
|---|---|---|---|
| 5,001,295 | 3/1991 | Angevine et al. | 585/467 |
| 5,292,934 | 3/1994 | Sikkenga et al. | 562/413 |
| 5,744,670 | 4/1998 | Motoyuki et al. | 585/320 |

FOREIGN PATENT DOCUMENTS 92-001142  4/1992  Japan .

*Primary Examiner*—Walter D. Griffin
*Assistant Examiner*—Thuan D. Dang
*Attorney, Agent, or Firm*—Oblon, Spivak, McClelland, Maier & Neustadt, P.C.

[57] ABSTRACT

2,6-Dialkylnaphthalene is prepared from a feedstock comprising naphthalene and an alkylating agent, by a process comprising the steps:

(I) transalkylating isomers of dialkylnaphthalene and naphthalene to produce monoalkylnaphthalene and isomers of dialkylnaphthalene;

(II) separating the product obtained in step (I) into naphthalene, monoalkylnaphthalene, dialkylnaphthalene and other components;

(III) alkylating the monoalkylnaphthalene fraction from step (II) with an alkylating agent to produce dialkylnaphthalene; and (IV) separating 2,6-dialkylnaphthalene from the dialkylnaphthalene fraction in step (II),
wherein at least step (I) or step (III) is conducted in the presence of a catalyst having a composition comprising a synthetic zeolite having an X-ray diffraction pattern with an interplanar d-spacing (Å)

12.36 ± 0.4
11.03 ± 0.2
8.83 ± 0.14
6.18 ± 0.12
6.00 ± 0.10
4.06 ± 0.07
3.91 ± 0.07
3.42 ± 0.06.

19 Claims, 9 Drawing Sheets

PROCESS FOR PREPARING DIALKYLNAPHTHALENE

BACKGROUND OF THE INVENTION

1. Field of the Invention

The present invention relates to a process for preparing alkylnaphthalene, and particularly to a method for preparing 2,6-dimethylnaphthalene (DMN) from naphthalene (NL) with an alkylating agent in the presence of a catalyst in both transalkylation and isomerization of DMN, as well as in alkylation of monomethylnaphthalene (MMN). This process is hereinafter described specifically in terms of the preparation of 2,6-DMN; however, this process can be extended to any dialkylnaphthalene.

DESCRIPTION OF THE BACKGROUND

The compound 2,6-DMN is used as a precursor for 2,6-naphthalenedicarboxylic acid which is used in the manufacture of polyester resins such as polyethylenenaphthalate (PEN) and polybutylenenaphthalate (PBN), because 2,6-DMN is easily oxidized to 2,6-naphthalenedicarboxylic acid in comparison to other precursors such as 2,6-diisopropylnaphthalene or 2-methyl-6-isobutylnaphthalene.

Many applications are expected for PEN including the manufacture of films and bottles and also in the preparation of long playing video films, advanced photosystems, hot fill containers, refillable bottles and tire cords, because of its good physical properties of strength, and thermal resistance, and because it is a good gas barrier. Uses expected for PBN'S include electronic and insulator applications as well as in the manufacture of auto parts. However, PEN and PBN are too expensive to permit expanded use because of few effective processes for commercially preparing 2,6-DMN.

Many processes have been proposed for preparing 2,6-DMN.

U.S. Pat. No. 4,795,847 (Weitkamp et al) describes a process for the preparation of 2,6-dialkylnaphthalene by alkylating naphthalene or 2-alkyl-naphthalene with an alkylating agent in the presence of a zeolite (specifically ZSM-5) as a catalyst.

U.S. Pat. No. 5,001,295 (Angevine et al) describes a process for preparing DMN by using 2-MMN as a feedstock and a synthetic zeolite (MCM-22) as a catalyst, and it shows MCM-22 is more effective than ZSM-5 in alkylation of 2-MMN.

However, these known processes provide only unit operations for the alkylation of 2-MMN which is an expensive feedstock and is not available in large amounts commercially. In addition, there is no description concerning how to use the DMN mixture (2,6-lean-DMN) after separation of 2,6-DMN, and the productivity of 2,6-DMN is not sufficient for mass production.

To increase the productivity of 2,6-DMN, it is preferred to use and isomerize 2,6-lean-DMN to enrich 2,6-DMN in DMN isomers.

In order to utilize the 2,6-lean-DMN isomers effectively, Japanese Pat. Laid Open No.4-1142 shows a process which recycles the 2,6-lean-DMN isomers for isomerization, and combines transalkylation between the 2,6-lean-DMN isomers with naphthalene to produce MMN. The MMN is alkylated with an alkylating agent to produce DMN.

This process consists of 5 steps (1)–(5) which are:

(1) (transalkylation and isomerization based on a modified ZSM-5 as a catalyst) DMN+NL→MMN DMN filtrate→2,6-rich-DMN isomers;

(2) (separation of the product of the 1 st step into naphthalene, MMN and DMN by distillation);

(3) (methylation of MMN using a methylating agent to produce DMN) MMN+methyl unit→DMN;

(4) (separation of the product of the 3rd step into MMN and DNM by distillation; and (5) (separation of 2,6-DMN from the DMN mixture of the second step and the 4th step by cooling crystallization).

According to the process, 2,6-lean-DMN isomers can be enriched to 2,6-DMN at least to some extent. However, the yield of 2,6-DMN is still low.

The reasons for the low yields of 2,6-DMN in the conventional process is believed to be based on the following two difficulties:

(I) Difficulty of Effective Isomerization

Ten isomers of DMN can be categorized into the following four groups (i)–(iv).

(i)   1,4-DMN ⇌ 1,3-DMN ⇌ 2,3-DMN
(ii)  1,5-DMN ⇌ 1,6-DMN ⇌ 2,6-DMN
(iii) 1,8-DMN ⇌ 1,7-DMN ⇌ 2,7-DMN
(iv)  1,2-DNM

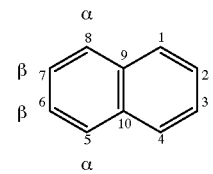

Isomerization within each group easily occurs; however, an isomerization between isomers in different groups is very difficult to conduct. Specifically, the polarity of the naphthalene molecule allows methyl-transition between the α-position and the β-position (e.g. 1,5-DMN⇌1,6-DMN). However, transition between a β-position and a β-position (e.g. 2,6-DMN⇌2,7-DNN) within the ring does not easily occur. Therefore, the isomerization of 2,6-lean-DMN isomers is not an effective way to enrich 2,6-DNM. In the above-mentioned Japanese Pat. Laid-Open Application No. 4-1142, low catalyst performance in the transalkylation and the alkylation causes the low separation yield of 2,6-DMN from DMN isomers.

Therefore, it is very important to use a catalyst which exerts high selectivity to 2,6-DMN in isomerization.

(II) Difficulty in Separation of 2,6-DMN from DMN Isomers

It is very difficult to separate 2,6-DMN from other isomers by conventional separation methods such as distillation or cooling crystallization because of the presence of 2,7-DMN.

In distillation, 2,6-DMN and 2,7-DMN can not be separated from each other because the difference in boiling point between 2,6-DMN and 2,7-DMN is only 0.3° C.

As for cooling crystallization, since 2,6-DMN and 2,7-DMN form a eutectic crystal at the weight ratio of 0.7(2,6-DMN/2,7-DMN), only a low yield of 2,6-DMN is achieved, For example, according to the above-mentioned Japanese Pat. Laid-Open No. 4-1142, the ratio of 2,6-DMN/2,7-DMN is 1.0. Therefore, the yield of 2,6-DMN is not high. The theoretical separation yield (Recovery of 2,6-DMN, which is the content of 2,6-DMN in the crystal versus the content of 2,6-DMN in the feedstock) is given by the following equation:

$$\eta = (1 - 0.7 \times (1/k)) \times 100$$

wherein "k" is 2,6-DMN/2,7-DMN ratio in crystallizer feed. Furthermore, the cooling of a DMN isomer mixture solution for 2,6-DMN purification forms a precipitate of very fine 2,6-DMN crystals in suspension, which make separation of 2,6-DMN extremely difficult.

Consequently it is very important to increase the ratio of 2,6-DMN/2,7-DMN for a higher yield of 2,6-DMN.

SUMMARY OF THE INVENTION

Accordingly, one object of the present invention is to provide a process for preparing useful alkylnaphthalene such as 2,6-DMN in high yield.

Briefly, this object and other objects of the present invention as hereinafter will become more readily apparent can be attained in a process for producing 2,6-dialkylnaphthalene from a feedstock comprising naphthalene and an alkylating agent comprising the following steps:

(I) transalkylating isomers of dialkylnaphthalene and naphthalene to produce monoalkylnaphthalene, and isomerization of dialkylnaphthalene isomers, (II) separating the product from said step (I) into naphthalene, monoalkylnaphthalene, dialkylnaphthalene and other components, (III) alkylating the monoalkylnaphthalene fraction from step (II) with an alkylating agent to produce dialkylnaphthalene, and (IV) separating 2,6-dialkylnaphthalene from the dialkylnaphthalene fraction in step (II), wherein at least step (I) or step (III) is conducted in the presence of a catalyst comprising a synthetic zeolite having an X-ray diffraction pattern with an interplanar d-spacing (Å)

| |
|---|
| 12.36 ± 0.4 |
| 11.03 ± 0.2 |
| 8.83 ± 0.14 |
| 6.18 ± 0.12 |
| 6.00 ± 0.10 |
| 4.06 ± 0.07 |
| 3.91 ± 0.07 |
| 3.42 ± 0.06. |

BRIEF DESCRIPTION OF DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION OF THE PREFERRED EMBODIMENTS

The present invention of increasing the yield of 2,6-DMN is based on the finding that the ratio of 2,6-DMN/2,7-DMN can be increased to more than 1.2 by employing a particular catalyst in a reaction such as alkylation, transalkylation and isomerization to enrich 2,6-DMN in DMN isomers.

The particular catalyst is a zeolite which comprises a synthetic porous crystalline material having an X-ray diffraction pattern including interplanar d-spacing as set forth in Table A.

TABLE A

| interplanar d-spacing (Å) | relative intensity $I/I_0 \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

*The relative intensities are given in terms of the symbols;
W = weak, M = medium, S = strong, VS = very strong.

The zeolite is known as MCM-22 and the entire contents of U.S. Pat. No. 5,001,295 are incorporated herein by reference.

The present invention provides a process for producing 2,6-DMN from a feedstock comprising naphthalene and an alkylating agent by utilizing the catalyst MCM-22, comprising:

step (I) transalkylating isomers of DMN in the presence of naphthalene to produce MMN, and isomerizing DMN.

step (II) separating the product in said step (I) into naphthalene, MMN, DMN and other components, step (III) alkylating the MMN fraction from step (II) using an alkylating agent to produce DMN, and step (IV) separating 2,6-DMN from the DMN fraction in said step (II).

Figure 1:
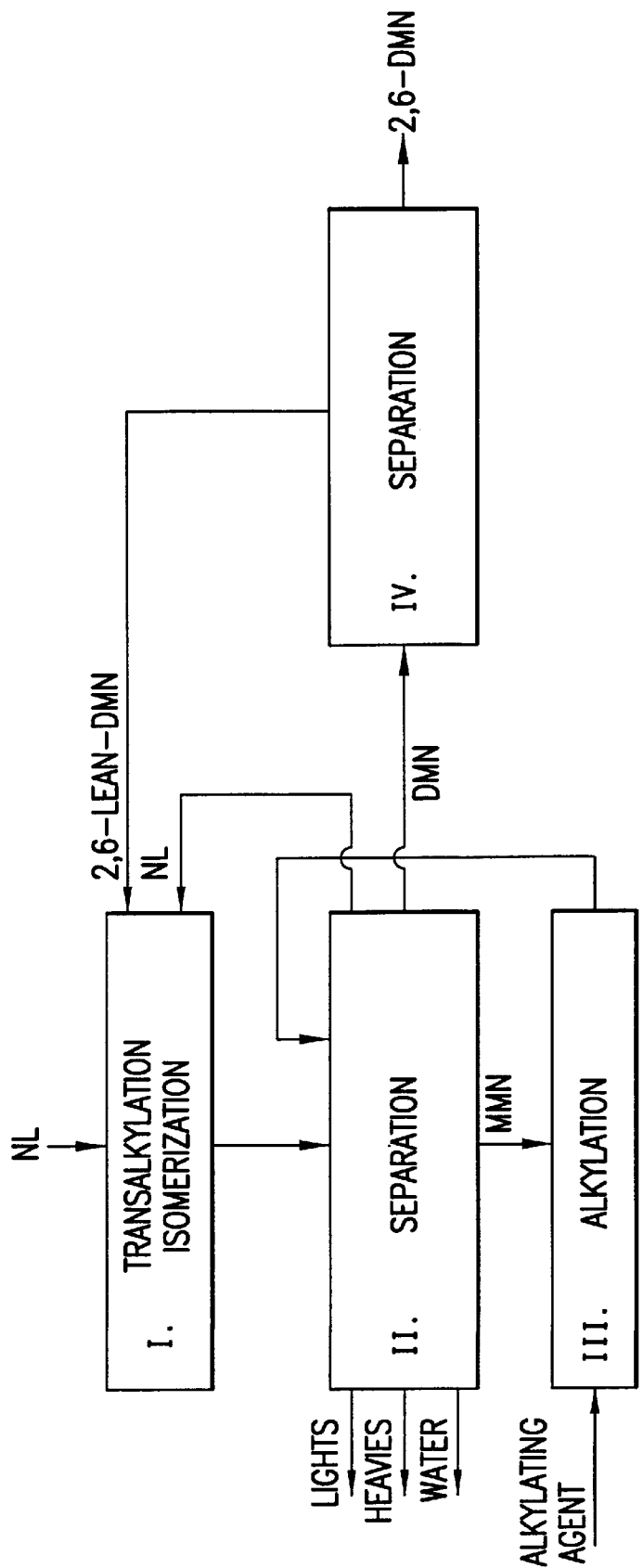
FIG. 1 is a schematic diagram which shows process steps which can be employed for this invention.

In this process, as illustrated in FIG. 1, the naphthalene fraction in step (II) is recycled to step (I), the product of step (III) is recycled to step (II), and the DMN fraction, after 2,6-DMN is separated therefrom in step (IV) is recycled to step (I).

The conditions of transalkylation and isomerization in step (I) include a temperature of about 0 to 500° C., and preferably 200 to 450° C., and a pressure of 0 to 250 atmospheres and preferably 1 to 25 atmospheres. The mole ratio of naphthalene to DMN can be from about 10:1 to 1:10, preferably from 5:1 to 1:5. The reaction is suitably accomplished utilizing a feed space velocity of about 0.1 to 10.0 $hr^{-1}$.

As a method for separation of step II, distillation can be employed. Other components, such as water, Lights and Heavies can be removed. In this specification, Lights mean components that have a lower boiling point than naphthalene such as methane, propane, benzene, and the like. Heavies mean components other than DMN, especially polyalkylnaphthalenes which have more than two alkyl groups such as trimethylnaphthalene, tetramethylnaphthalene, and so on.

The conditions of alkylation in step III include a temperature of about 0 to 500° C., and preferably 240 and 450° C., and a pressure of between 0 to 250 atmospheres and preferably 1 to 50 atmospheres. The mole ratio of alkylating agent to MMN can be from about 20:1 to 1:20, preferably from 10:1 to 1:10. The reaction is suitably accomplished utilizing a feed space velocity of about 0.1 to 10.0 hr$^{-1}$.

Preferred alkylating agents include alcohols, olefins, aldehydes, halides, and ethers. For example, methanol, dimethylether and polyalkylbenzene are preferred. Methanol and dimethylether are especially preferred.

The alkylation can be carried out in any of the known reactors usually employed for alkylation. For example, a tubular reactor with a downflow of reactants over a fixed bed of catalyst can be employed.

As for the separation in step (IV), any method for separation of isomers such as cooling crystallization or adsorption can be used. However, in order to obtain high yields of 2,6-DMN, crystallization under high pressure (High Pressure Crystallization) is preferred. Therefore, the use of crystallization under high pressure is recommended in step (IV) in whole or in part.

In general, a liquid mixture containing two or more substances is pressurized, and a certain substance in the mixture is solidified and separated from the residual liquid by the effect of the pressure. In other words, this method involves a separating and purifying technique wherein a liquid mixture containing two or more substances is placed in a tightly sealed pressure vessel, a portion of the desired substance, 2,6-dimethylnaphthalene, is solidified to form a solid-liquid co-existing state, the liquid is discharged from the co-existing system while maintaining the pressure of the solid-liquid coexisting system at a higher level than equilibrium pressure of the objective substance, then the solid remaining in the vessel is pressed for discharging the residual liquid between the solid particles and integrating the solid particles. This technique is generally described in U.S. Pat. No. 5,220,098.

The method involves injecting the slurry or liquid into a high pressure vessel for conducting crystallization under high pressure; adiabatically pressurizing the vessel to a pressure of from 300 to 4,000 kgf/cm$^2$, preferably 500 to 2,000 kgf/cm$^2$ to increase the quantity, i.e. the amount of 2,6-dimethylnaphthalene crystals, whereby coexistence of solid-liquid phases exist at the high pressure conditions; discharging the liquid phase component from the high pressure vessel, the discharging being conducted under pressure, to increase the ratio of the solid phase relative to the liquid phase within the vessel; lowering the pressure of the residual liquid phase so as to dissolve partially and purify the solid phase; discharging the residual liquid phase by applying pressure to the solid phase within the high pressure vessel whereby a 2,6-dimethylnaphthalene crystal block having a high purity is obtained within the high pressure vessel. By this technique, a purity of 2,6-dimethylnaphthalene of ≧98% by weight, preferably ≧99% by weight may be obtained.

In the transalkylation and isomerization of the present invention, 2,6-lean-DMN, which contains less than 11 weight % of 2,6-DMN in the isomers is preferred. More preferably the content of 2,6-DMN in the 2,6-lean-DMN stream should be less than 9%.

As mentioned above, a high ratio of 2,6-DMN/2,7-DMN is required in order to obtain a high yield of 2,6-DMN. According to the present invention, the ratio of 2,6-DMN/2,7 DMN can be more than 1.2 in step (I) and can be more than 1.1 in step (III).

Further, the performance of the catalyst in isomerization can be evaluated by a molar ratio of the 2,6-DMN content in the total DMN after isomerization against the 2,6-DMN content in the total DMN before isomerization. According to the present invention, this ratio can be more than 1.5.

It is also noted that the ratio of 2-MMN to 1-MMN in MMN isomers produced in step I should be as high as possible because a higher 2-MMN/1-MMN ratio gives a higher 2,6-DMN yield at alkylation. Theoretically, the ratio is said to be around 2.2, however, it is difficult to achieve such a high ratio in the conventional process. According to the present invention, the ratio can be more than 2.0 in transalkylation and isomerization by using MCM-22 as the catalyst.

Figure 2:
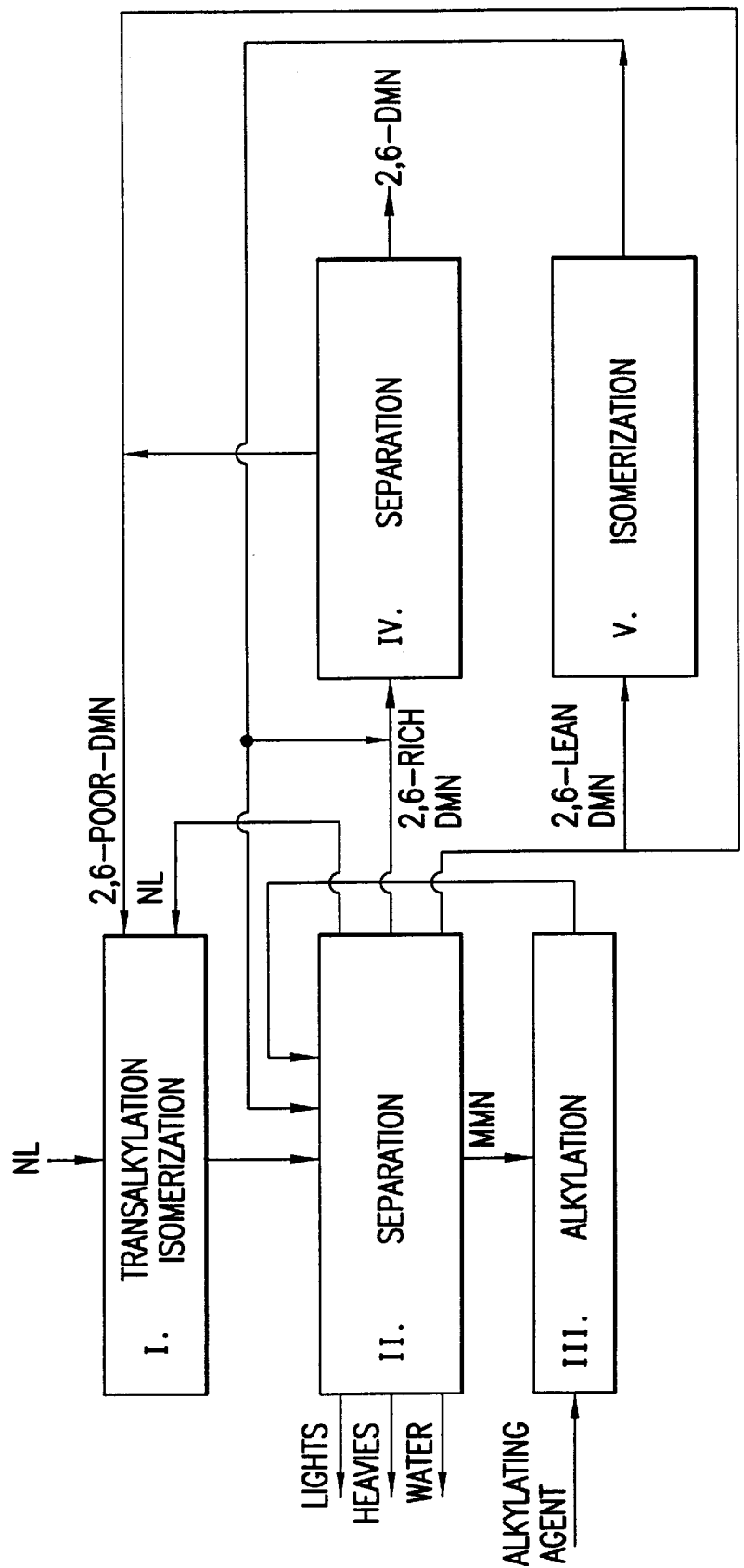
FIG. 2 shows a preferred embodiment of the invention wherein 2,6-lean-DMN from step (II) is isomerized and recycled in the process.
Figure 3:
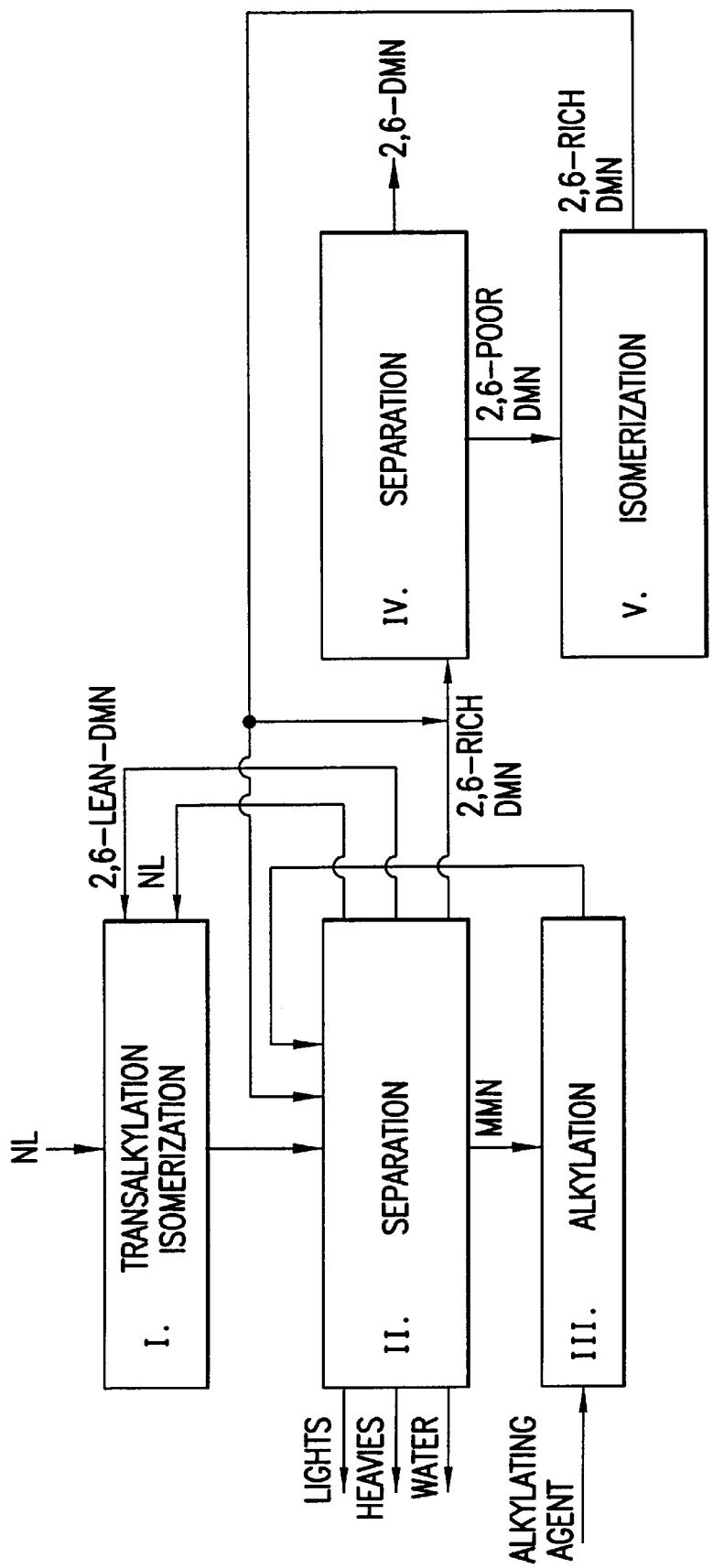
FIG. 3 shows a preferred embodiment of the invention wherein 2,6-lean-DNW from step (IV) is isomerized and recycled in the process.

FIG. 2 and FIG, 3 show preferred embodiments of this invention, wherein the DMN fraction is separated into 2,6-rich-DMN and 2,6-lean-DMN, and the 2,6-rich-DMN is utilized in separating 2,6-DMN in step (IV). In the process of FIG. 2, a part of the 2,6-lean-DMN is isomerized in the presence of the catalyst MCM-22, and recycled to step (II) or step (IV). In the process of FIG. 3, DMN isomers after 2,6-DMN is separated in step (IV) are utilized in the isomerization, and 2,6-rich-DMN after isomerization is recycled to step (II) or step (IV).

The conditions of isomerization in step (V) in FIG. 2 and FIG. 3 include a temperature of about 0 to 500° C., preferably 150 and 350° C., and a pressure of 0 to 250 atmospheres, preferably 1 to 25 atmospheres. The reaction is suitably accomplished utilizing a feed space velocity of about 0.1 to 10.0 hr$^{-1}$.

Figure 4:
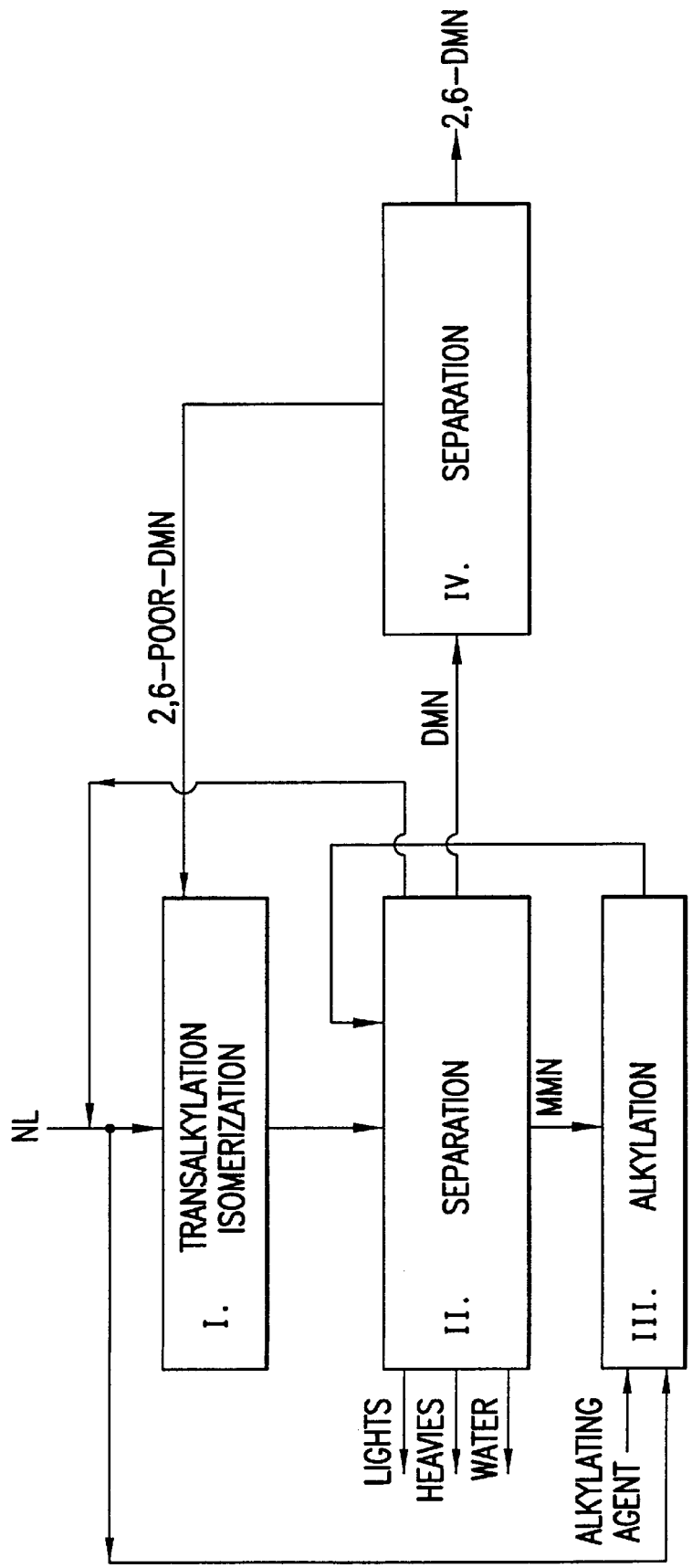
FIG. 4 shows a preferred embodiment of the invention wherein naphthalene is fed to step (III)

FIG. 4 shows another preferred embodiment of this invention, wherein naphthalene is fed into step III. The molar ratio of naphthalene to monoalkylnaphthalene fed into step (III) can be from about 1:3 to 3:1.

Figure 5:
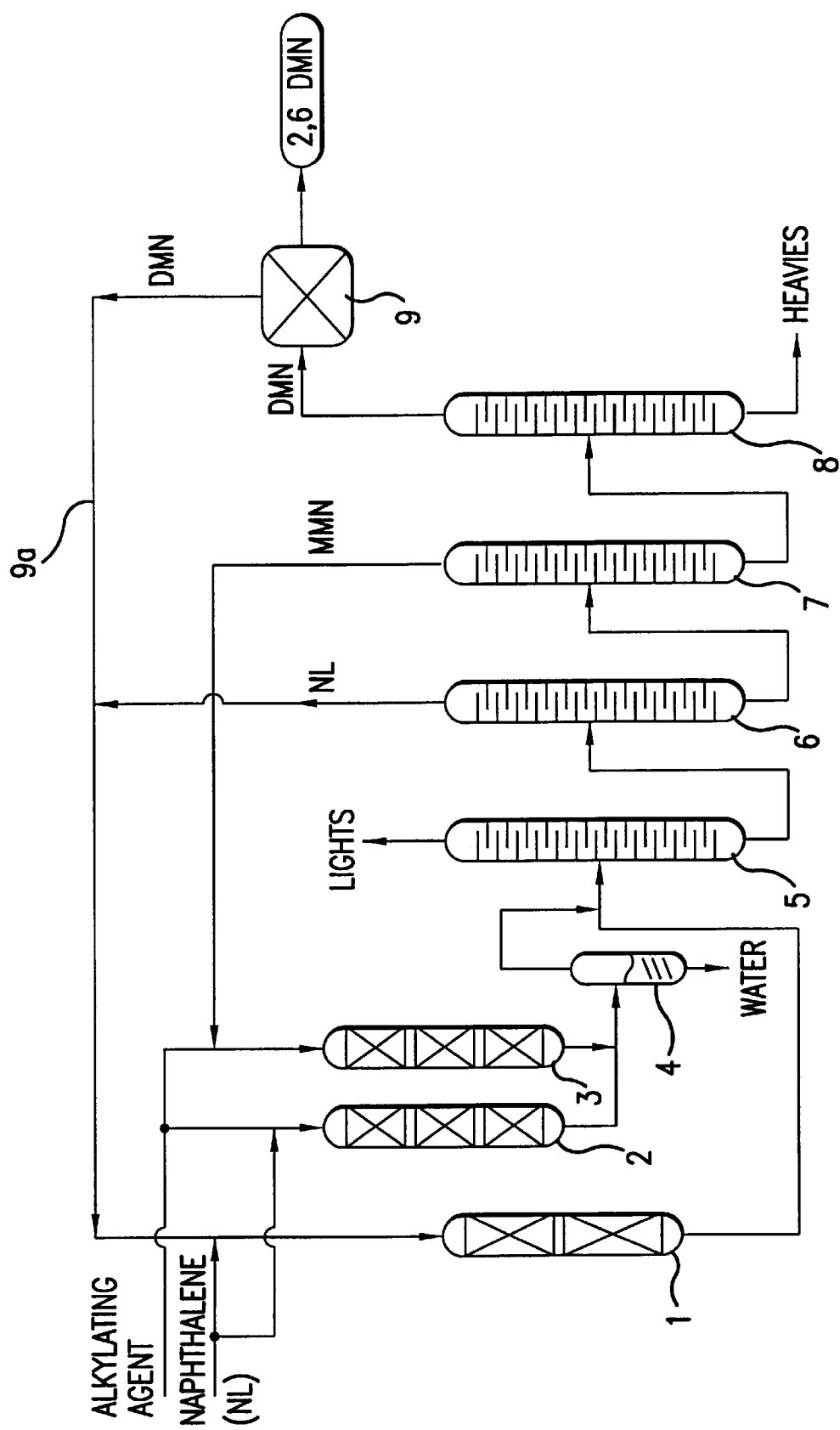
FIG. 5 is a flow sheet of a preferred embodiment showing the process steps in FIG. 1.

FIG. 5 is a flowchart of a preferred embodiment showing the process of the present invention. In FIG. 5, 1 is a reactor for transalkylation and isomerization, 2 and 3 are reactors for alkylation, 4 is a separator of water, 5–8 are distillers, and 9 is a crystallizer.

In continuous operation, naphthalene and DMN isomers are introduced into reactor 1. In reactor 1, MMN is produced by the transalkylation between naphthalene and DMN. At the same time DMN isomers are isomerized and the content of 2,6-DMN increases in reactor 1. The product is fed into the distiller 5, Lights are separated therein, and the other components are fed into distiller 6. In distiller 6, naphthalene is separated and cycled back to reactor 1, and the other components are fed into distiller 7. MMN is separated in distiller 7 and fed to reactor 3, and the other components are fed into distiller 8. In distiller 8, DMN is separated from Heavies and fed into crystallizer 9 and 2,6-DMN is separated from DMN isomers. DMN isomers other than 2,6-DMN are separated therefrom and are called 2,6-lean-DMN which is recycled to reactor 1 through stream No. 9a.

In reactor 3, MMN from the distiller 7 and an alkylating agent such as methanol are mixed in the presence of the catalyst, and DMN is produced by way of alkylation of MMN. In the event methanol is used as the alkylating agent, the product is fed into water separator 4 and fed to the distillers. When dimethylether is used as the alkylating agent, water separator 4 can be left out of the process.

In starting up the process, reactor 2 is utilized for alkylation of naphthalene to produce MMN and DMN in the presence of the catalyst, and the product is also fed into water separator 4 to eliminate water. After water is removed, the components from water separator 4 are fed to distillers 5–8, and the above mentioned continuous operations are conducted.

Figure 6:
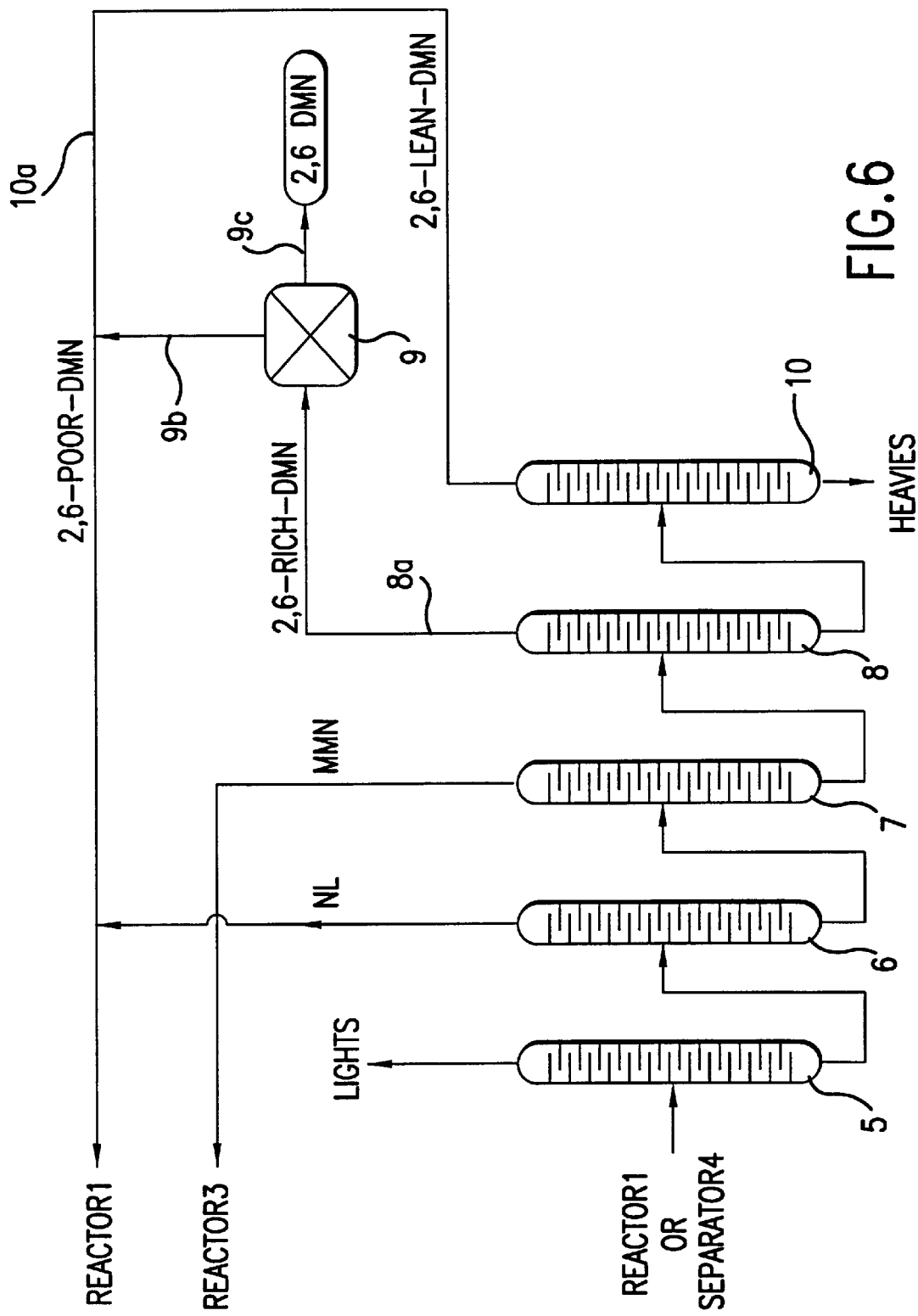
FIG. 6 is a flow sheet of a preferred embodiment showing the process steps in which the DMN fraction is separated into 2,6-rich DMN and 2,6-lean DMN before step (IV) in FIG. 1.

It should be noted that there are ten kinds of isomers in DMN. The boiling points of the isomers are different from each another and the boiling point of 2,6-DMN is the lowest. Therefore, in order to obtain a higher yield of 2,6-DMN, it is preferred to separate DMN isomers into 2,6-rich DMN and 2,6-lean DMN by distillation and only the 2,6-rich DMN is utilized for crystallization to produce 2,6-DMN as shown in FIG. 6.

The bottom fraction from distiller 7 is introduced to distiller 8 in which 2,6-rich-DMN is separated from the top and fed to crystallizer 9 via stream No. 8a. 2,6-rich-DMN is separated into 2,6-DMN and 2,6-lean-DMN, 2,6-DMN is obtained as a product through stream No. 9c, and the 2,6-lean-DMN is fed back to reactor 1 via stream No. 9b.

The bottoms fraction from distiller 8 is introduced to distiller 10 and is separated into 2,6-lean-DMN and Heavies. The 2,6-lean-DMN can be recycled for isomerization in reactor 1 through stream No. 10a.

Figure 7:
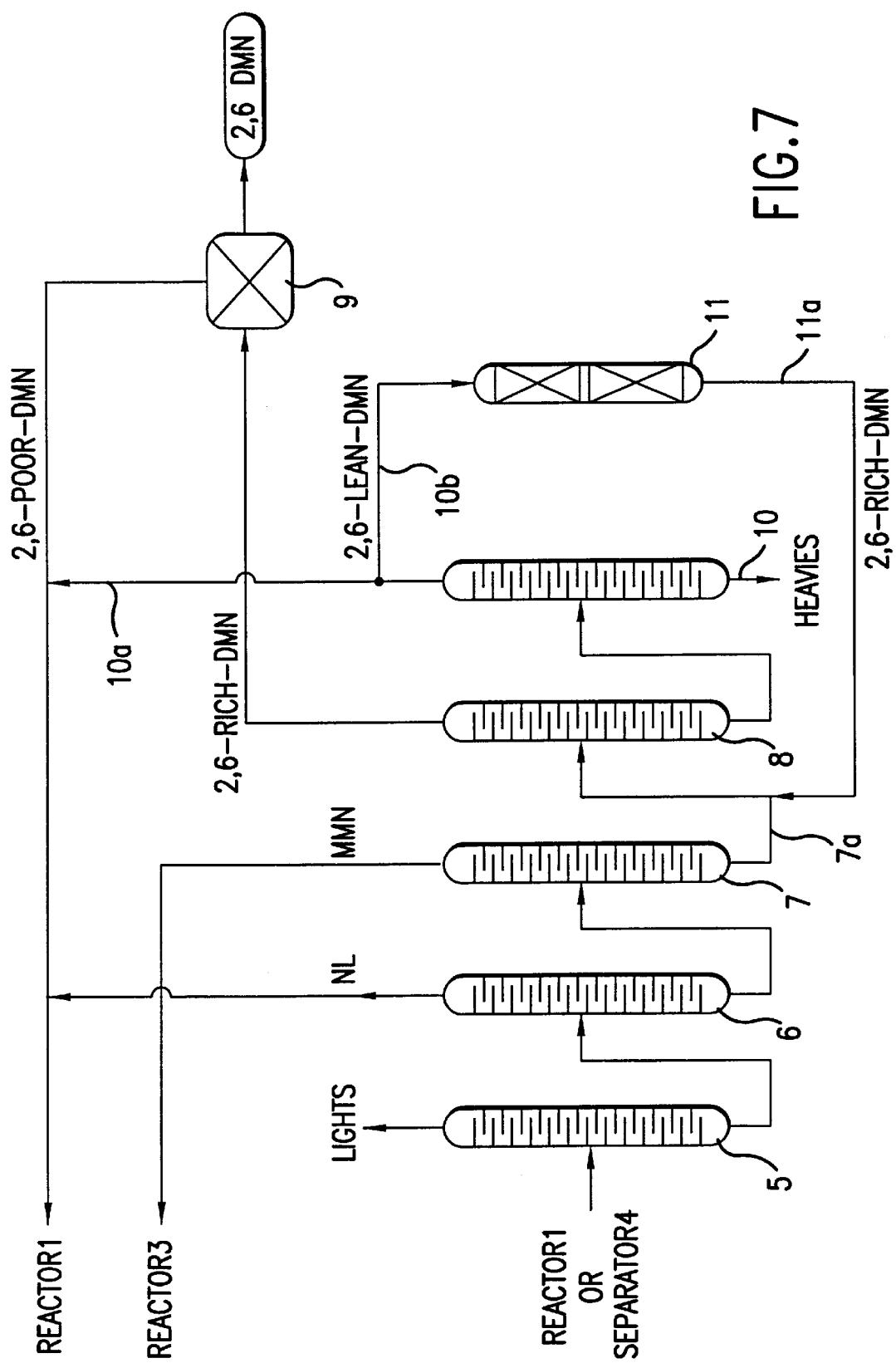
FIG. 7 shows a schematic representation of a preferred embodiment in accord with the process in FIG. 2.

More preferably, a part of the 2,6-lean-DMN is isomerized in the presence of the catalyst to increase the ratio of 2,6-DMN in the DMN isomers as shown in FIG. 7. In FIG. 7, the DMN fraction is separated into 2,6-rich-DMN and 2,6-lean-DMN, the 2,6-rich-DMN is utilized in separating 2,6-DMN in step (IV) as in a similar manner with FIG. 6. Some part of the 2,6-lean-DMN is introduced into reactor 11 for isomerization via stream No. 10b. The rest is recycled to reactor 1 via stream No. 10a. 2,6-rich-DMN after isomerization is recycled to stream No. 7a via stream No. 11a.

Figure 8:
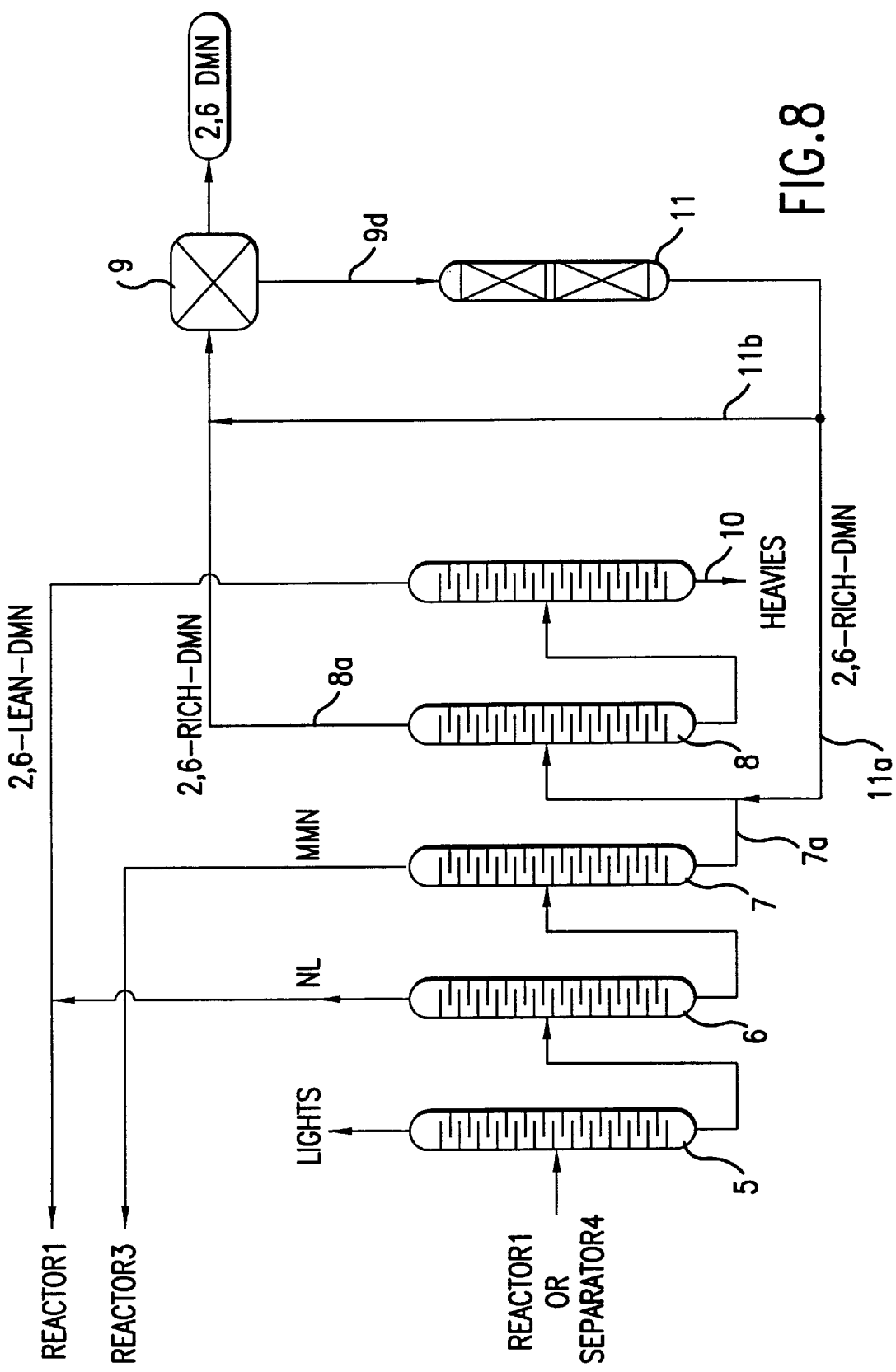
FIG. 8 shows a schematic representation of a preferred embodiment in accord with the process in FIG. 3.

FIG. 8 shows another preferred embodiment of the invention, wherein DMN isomers other than 2,6-DMN are separated in crystallizer 9. The material largely containing other DMN isomers is fed into a reactor 11 via stream No. 9d. 2,6-Rich-DMN after isomerization is recycled to stream No. 7a via stream No. 11a or recycled to stream No. 8a via stream No. 11b.

Figure 9:
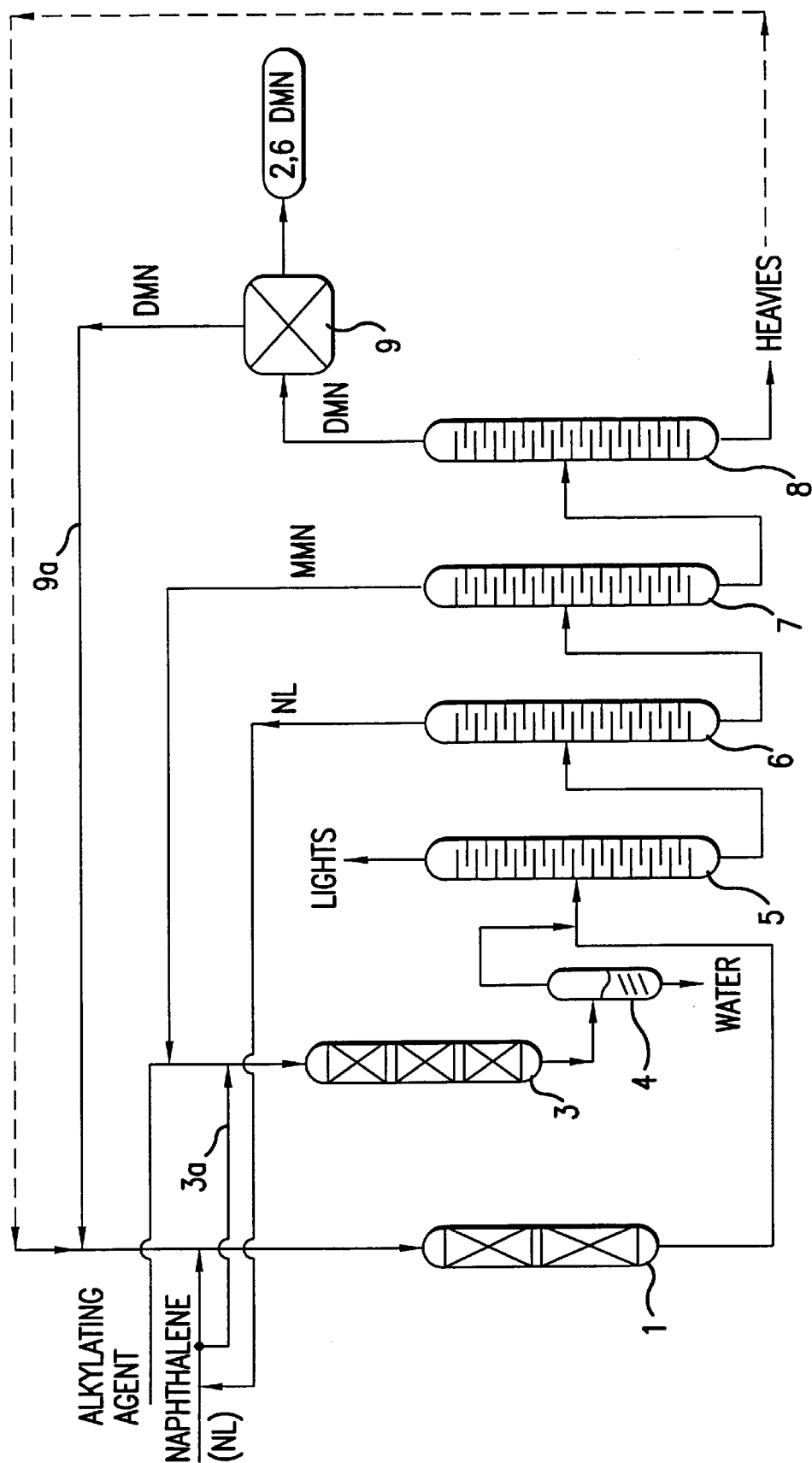
FIG. 9 shows a schematic representation of a preferred embodiment in accord with the process in FIG. 4.

FIG. 9 also shows another preferred embodiment of the invention, wherein naphthalene is fed into a reactor 3 via stream No. 3a. Naphthalene and an alkylation agent and MMN, are combined in a process scheme that does not contain reactor 2 described in FIG. 5.

The remainder of the process described in FIGS. 6, 7 and 8 can be carried out in a similar fashion to that described in detail for the embodiments of FIGS. 5 and 9.

Furthermore, the process embodiments of FIGS. 6, 7, 8 and 9, Heavies can be recycled to reactor 1 for transalkylation to produce MMN or DMN.

As described above, according to the present invention, the yield of 2,6-DMN can be increased in comparison to that which can be achieved by the conventional processes. The 2,6-DMN prepared by the present process can be used in a process of preparing a polyethylenenaphthalate polymer (PEN polymer) by the steps of oxidizing 2,6-DMN to form 2,6-naphthalene-dicarboxylic acid (2,6-NDA), or oxidizing and esterifying 2,6-DMN to form an ester of 2,6-NDA, and condensing said 2,6-NDA or ester thereof with ethylene glycol to form the PEN polymer.

Further, the 2,6-DMN also prepared by the present process can be used in a process of preparing a polybutylenenaphthalate polymer (PBN polymer) by the steps of oxidizing 2,6-DMN to form 2,6-naphthalene-dicarboxylic acid (2,6-NDA), or oxidizing and esterifying 2,6-DMN to form an ester of 2,6-NDA, and condensing said 2,6-NDA or ester thereof with butanediol to form the PBN polymer.

Having generally described this invention, a further understanding can be obtained by reference to certain specific examples which are provided herein for purposes of illustration only and are not intended to be limiting unless otherwise specified.

EXAMPLE 1

(transalkylation and isomerization)

A 30 g amount of MCM-22 (1/16"D×3/8"L, cylindrical pellet) are charged into a tubular reactor (volume: 122 cc). The reactor is heated from room temperature to 400° C. at the rate of 100° C. /hr while introducing nitrogen gas into the reactor at atmospheric pressure.

As a feedstock for transalkylation and isomerization, isomers of DMN and naphthalene are mixed in a molar ratio of 1:1. The weight % of isomers of DMN are shown in Table 1.

TABLE 1

(Feedstock)

| Component | weight % |
|---|---|
| dimethylnaphthalene | 99.70 |
| 2,6-DMN | 6.21 |
| 2,7-DMN | 8.63 |
| other isomers | 84.86 |
| monomethylnaphthalene | 0.30 |
| 2-MMN | 0.17 |
| 1-MMN | 0.13 |

The feedstock is introduced into the reactor at the rate of 30 g/hr for 8 hours, and the product obtained is analyzed by gas chromatography. Table 2 shows the analysis of the components of the feedstock and the product.

TABLE 2

(Transalkylation and Isomerization)

|  |  | before reaction | after reaction |
|---|---|---|---|
|  | Component (wt. %) |  |  |
| * | dimethylnaphthalene | 53.19 | 39.41 |
|  | 2,6-DMN | 3.30 | 6.65 |
|  | 2,7-DMN | 4.59 | 4.59 |
| * | other isomers | 45.30 | 28.17 |
|  | monomethylnaphthalene | 0.10 | 17.59 |
| * | 2-MMN | 0.01 | 12.16 |
|  | 1-MMN | 0.09 | 5.43 |
| * | naphthalene | 46.71 | 38.15 |
|  | other component | 0 | 4.85 |
| evaluation |  |  |  |
| 2,6-DMN/total DMN (%) |  | 6.2 ---① | 16.9 ---② |
| 2,6-DMN/2,7-DMN |  | 0.72 | 1.45 |
| content of 2,6-DMN (after/before): @ 1 |  | — | 2.73 |
| NL conversion (%) |  | — | 18.3 |
| DMN conversion (%) |  | — | 25.9 |
| produced MMN/(converted DMN × 2): @ 2 |  | — | 0.70 |
| 2-MMN/1-MMN |  | — | 2.23 |

@1 The ratio of ②/① in 2,6-DMN/total DMN.
@2 Amounts are calculated on a molar basis.

As can be seen in Table 2, the ratio of 2,6-DMN/2,7-DMN is over 1.2 and the ratio of 2-MMN is over 2.0.

EXAMPLE 2

(Transalkylation and Isomerization)

The same experiment as described in Example 1 is conducted except that the molar ratio of DMN to naphthalene is 5:1. Feedstock and product analysis are shown in Table 3.

TABLE 3

(Transalkylation and Isomerization)

| | before reaction | after reaction |
|---|---|---|
| Component (wt %) | | |
| dimethylnaphthalene | 84.37 | 65.91 |
| 2,6-DMN | 5.22 | 11.39 |
| 2,7-DMN | 7.28 | 7.42 |
| other isomers | 71.87 | 47.10 |
| monomethylnaphthalene | 0.17 | 13.81 |
| 2-MMN | 0.02 | 9.54 |
| 1-MMN | 0.15 | 4.27 |
| naphthalene | 15.46 | 12.65 |
| other component | 0 | 7.63 |
| evaluation | | |
| 2,6-DMN/total DMN (%) | 6.2 --- ① | 17.3 --- ② |
| 2,6-DMN/2,7-DMN | 0.72 | 1.53 |
| content of 2,6-DMN (after/before): @ 1 | — | 2.79 |
| NL conversion (%) | — | 18.2 |
| DMN conversion (%) | — | 21.9 |
| produced MMN/(converted DMN × 2): @ 2 | — | 0.41 |
| 2-MMN/1-MMN | — | 2.2 |

@1 The ratio of ②/① in 2,6-DMN/total DMN
@2 Amounts are calculated on a molar basis.

As can be seen from Table 3, the ratio of 2,6-DMN/2,7-DMN is over 1.2 and the ratio of 2-MMN/1-MMN is over 2.0.

EXAMPLE 3

(alkylation)

A 153 g amount of MCM-22 is charged into a tubular reactor (volume: 370 cc). As a feedstock for alkylation, 1-MMN (purity 95.5%) and 2-MMN (purity 96.6%) are used, and mixed at a molar ratio of 2.2 of 2-MMN/1-MMN. Feedstock is supplied in the reactor (350° C.) at the rate of 76.7 g/hr and 0.5 hr$^{-1}$ in WHSV for 4 hours with a feed of hydrogen gas at a rate of 0.9 ft$^3$/hr. Thereafter, methanol is supplied to the reactor at the rate of 17.3 g/hr and the reaction is allowed to proceed for 20 hours. The product obtained is analyzed by gas chromatography, and the results are summarized in Table 4.

TABLE 4

(alkylation)

| | before reaction | after reaction |
|---|---|---|
| Component (wt %) | | |
| dimethylnaphthalene | 0 | 35.45 |
| 2,6-DMN | 0 | 5.12 |
| 2,7-DMN | 0 | 4.44 |
| other isomers | 0 | 25.89 |
| monomethylnaphthalene | 98.66 | 41.16 |
| 2-MMN | 67.61 | 28.84 |
| 1-MMN | 31.05 | 12.32 |
| naphthalene | 0 | 0.19 |
| other component | 1.53 | 23.20 |

TABLE 4-continued (alkylation)

| | before reaction | after reaction |
|---|---|---|
| evaluation | | |
| 2-MMN/1-MMN | 2.2 | 2.3 |
| MMN conversion (%) | — | 58.28 |
| 2,6-DMN/total DMN (%) | — | 14.45 |
| 2,6-DMN/2,7-DMN | — | 1.16 |

As can be seen from Table 4, the ratio of 2,6-DMN/2,7-DMN is over 1.1 and the ratio of 2-MMN/1-MMN is over 2.0.

EXAMPLE 4

(alkylation)

A 20 g amount of MCM-22 is charged into the tubular reactor (volume:200 cc). As a feedstock for alkylation, 1-MMN and 2-MMN are mixed in the molar ratio of 2,2 of 2-MMN/1-MMN, which mixture is used as a feedstock for alkylation.

The reactor is heated gradually from ambient temperature to 450° C. to dry the catalyst over a supply of nitrogen gas, and then the temperature in the reactor is decreased to 400° C. and the flow of nitrogen gas ceases when the temperature becomes stable at 400° C. Thereupon, the supply of feedstock is started in the reactor at the rate of 20 g/hr and 1.0$^{-1}$ in WHSV. One hour later, as an alkylating agent, methanol is introduced in the reactor at 4.4 g/hr, and the alkylation of MMN is carried out for 4 hours at a pressure of 5 kg/cm$^2$. The product obtained is analyzed by gas chromatography, and the results are summarized in Table 5.

TABLE 5

(Alkylation)

| | before reaction | after reaction |
|---|---|---|
| Component (wt %) | | |
| dimethylnaphthalene | 0 | 13.30 |
| 2,6-DMN | 0 | 1.58 |
| 2,7-DMN | 0 | 1.16 |
| other isomers | 0 | 10.56 |
| monomethylnaphthalene | 98.09 | 85.04 |
| 2-MMN | 66.65 | 56.89 |
| 1-MMN | 31.44 | 28.15 |
| naphthalene | 0.94 | 0.79 |
| other component | 0.97 | 0.87 |
| evaluation | | |
| 2-MMN/1-MMN | 2.2 | 2.0 |
| MMN Conversion (%) | — | 13.3 |
| 2,6-DMN/total DMN (%) | — | 11.9 |
| 2,6-DMN/2,7-DMN | — | 1.36 |

As can be seen from Table 5, the ratio of 2,6-DMN 2,7-DMN is over 1.1 and the ratio of 2-MMN/1-MMN is over 2.0.

EXAMPLE 5

(Separation)

(1) Crystallization under High Pressure Crystallization

A 1,505 g amount of DMN isomers is supplied into the high pressure crystallizer (KOBELCO 1.5L type), and 236 g of 2,6-DNN crystals (purity 87%) are separated under the condition of 2000 kgf/cm$^2$ and 45° C.

(2) Cooling Crystallization

Using a vessel for crystallization (3 liter), 2,001 g of DMN isomers is cooled quickly from 50° C. to 40° C. with slow stirring. Then, 0.5 g of seed crystals are charged to the vessel which is kept at a temperature at 40° C. for an hour. Thereupon, the feedstock is cooled to 10° C. at 2° C./min. A 360 g amount of 2,6-DMN crystals (purity 68%) is separated by filtration under pressure.

The results of separation by both crystallization under high pressure and cooling crystallization are summarized in Table 6.

TABLE 6

(Separation)

| Component (g) | before crystallization | crystal | filtrate |
|---|---|---|---|
| CRYSTALLIZATION UNDER HIGH PRESSURE | | | |
| 2,6-DMN | 301 | 205 | 96 |
| 2,7-DMN | 232 | 22 | 210 |
| other DMN | 972 | 9 | 963 |
| TOTAL | 1505 | 236 | 1269 |
| 2,6-DMN/2,7-DMN | 1.3 | — | 0.5 |
| 2,6-DMN/total DMN | 20.0% | — | 7.6% |
| purity of crystal | — | 87% | — |
| recovery of 2,6-DMN | — | 68% | — |
| yield of 2,6-DMN | — | 13.6% | — |
| COOLING CRYSTALLIZATION | | | |
| 2,6-DMN | 400 | 244 | 156 |
| 2,7-DMN | 308 | 67 | 241 |
| other DMN | 1293 | 49 | 1244 |
| TOTAL | 2001 | 360 | 1641 |
| 2,6-DMN/2,7-DMN | 1.3 | — | 0.65 |
| 2,6-DMN/total DMN | 20.0% | — | 9.5% |
| purity of crystal | — | 68% | — |
| recovery of 2,6-DMN | — | 61% | — |
| yield of 2,6-DMN | — | 12.2% | — |

"Recovery of 2,6-DMN" means the content of 2,6-DMN in the crystals against the content of 2,6-DMN in the feedstock.

"Yield of 2,6-DMN" means the content of 2,6-DMN in the crystal against the total weight of feedstock.

As shown in Table 6, the yield of 2,6-DMN by crystallization under high pressure is much higher than by cooling crystallization. Further, the 2,6-DMN/total-DMN ratio of the filtrate by crystallization under high pressure is less than 8%. Therefore, the filtrate is more effective as a feedstock for transalkylation and isomerization of 2,6-lean-DMN. Furthermore, when an attempt is made to increase the purity of crystals by cooling crystallization, the yield of 2,6-DMN decreases drastically.

EXAMPLE 6

(Alkylation, Distillation and Crystallization)

(1) Alkylation

A 150 g amount of MCM-22 were charged in the tubular reactor (volume:370 cc). As a feedstock for alkylation, 1-MMN and 2-MMN are mixed at the molar ratio of 2.2 of 2-MMN/1-MMN and used as a feedstock for alkylation The reactor is heated gradually from ambient temperature to 270° C. to dry the catalyst while supplying hydrogen gas. Thereupon, the feedstock is supplied to in the reactor at the rate of 150 g/hr and 1.0$^{-1}$ in WHSV. The temperature in the reactor is increased at 10° C./hr, when it reaches 375° C., methanol is introduced into the reactor at 33 g/hr. The alkylation of MMN is carried out for 10 days while supplying hydrogen gas at 1.7 ft$^3$/hr, and about 40 kg of product is obtained.

(2) Distillation

After water is removed from the product in the alkylation 16.5 kg of the dehydrated product is used for distillation by a batch type distiller. A number of theoretical steps of the distiller is 50 and the pressure is controlled to 49–50 Torr at the bottom and 20 Torr at the top. Distillation proceeds at a reflux ratio of 50 to 100.

The product is separated into seven fractions by differences in boiling points as shown in Table 7. The content of each fraction is also shown in Table 7.

TABLE 7

(Distillation)

| | Fr-1 | Fr-2 | Fr-3 | Fr-4 | Fr-5 | Fr-6 | Fr-7 |
|---|---|---|---|---|---|---|---|
| temperature (°C.) | –100 | 100–125 | 125–132 | 132–139 | 139–145 | 145– | residue |
| weight % | 9.7 | 32.1 | 18.1 | 8.5 | 11.8 | 5.0 | 12.4 |
| *content | | | | | | | |
| naphthalene | | 1.3 | 2.2 | 0.2 | | | |
| 2-MMN | | 71.0 | 50.3 | 6.0 | 0.3 | 0.1 | 0.3 |
| 1-MMN | | 27.2 | 31.9 | 6.5 | 0.4 | 0.2 | 0.1 |
| 2,6-DMN | | | 4.8 | 24.2 | 4.9 | 0.3 | |
| 2,7-DMN | | | 4.2 | 21.5 | 5.3 | 0.3 | |
| 1,6-DMN | | | 1.2 | 11.4 | 18.3 | 3.4 | 0.1 |
| 1,3-DMN + 1,7-DMN | | | 4.5 | 29.3 | 19.7 | 3.0 | |
| 1,4-DMN | | | | | 3.9 | 2.7 | |
| 1,2-DMN + 1,5-DMN | | | | | 39.0 | 71.3 | 6.2 |
| 2,3-DMN | | | | | 7.3 | 8.3 | 0.5 |
| 1,8-DMN | | | | | | | |
| Heavies | | | | 1.2 | 0.9 | 9.9 | (*1) 92.6 |
| other components | 0.5 | 0.9 | 0.9 | 0.9 | 0.9 | 0.5 | 0.2 |

Note (*1): Most of Heavies of fraction 7 (Fr-7) are trimethylnaphthalene and tetramethylnaphthalene.

(3) Crystallization

A mixture of Fr-4 and Fr-5 in Table 7 is utilized for crystallization. The concentration of 2,6-DMN in the mixture is increased to 71% by cooling crystallization at the temperature of 30° C., and then it is introduced into the high pressure crystallizer. Crystals of 2,6-DMN (97% in purity) are obtained by crystallization under high pressure under the conditions of 1500 kgf/cm$^2$ and 105° C. The amount of recovery of 2,6-DMN from the mixture of Fr-4 and Fr-5 is 60%.

EXAMPLE 7

(Isomerization)

A 25 g amount of MCM-22 is charged into the tubular reactor (volume: 200 cc). The reactor is heated gradually from ambient temperature to 400° C. to dry the catalyst while supplying nitrogen gas, and the flow of nitrogen gas is ceased when the temperature becomes stable at 400° C. Thereupon, 2,6-lean-DMN is supplied to the reactor at the rate of 25 g/hr and 1.0 hr$^{-1}$ in WHSV, and isomerization of DMN is carried out for four hours. The contents of the obtained product are analyzed by gas chromatography, and the results are summarized in Table 8.

TABLE 8

(Isomerization)

| Component (wt %) | before reaction | after reaction |
|---|---|---|
| dimethylnaphthalene | 98.09 | 80.10 |
| 2,6-DMN | 6.21 | 13.96 |
| 2,7-DMN | 8.48 | 8.66 |
| other isomers | 83.40 | 57.48 |
| monomethylnaphthalene | 0.20 | 9.77 |
| 2-MMN | 0.03 | 6.71 |
| 1-MMN | 0.17 | 3.06 |
| naphthalene | 0 | 0.78 |
| other component | 1.71 | 9.35 |
| evaluation | | |
| 2,6-DMN/total DMN (%) | 6.3 | 17.4 |
| 2,6-DMN/2,7-DMN | 0.73 | 1.61 |

As can be seen from Table 8, the ratio of 2,6-DMN/2,7-DMN is over 1.1.

EXAMPLE 8

(Transalkylation of Heavy Components)

A 20 g amount of MCM-22 is charged into a tubular reactor(volume: 200 cc). Heavy components, which are obtained in Example 6, and naphthalene are mixed at a ratio (naphthalene/heavy) of 0.2 in weight and used as a feedstock.

The reactor is heated gradually from ambient temperature to 400° C. to dry the catalyst while supplying nitrogen, and the flow of nitrogen gas ceases when the temperature becomes stable at 400° C. Thereupon, the feedstock is supplied to the reactor at the rate of 20 g/hr and $1.0^{-1}$ in WHSV. Transalkylation of the heavy components is carried out for 4 hours at a pressure of 5 kg/cm$^2$ at 350° C. The product obtained is analyzed by gas chromatography and the results are summarized in Table 9.

TABLE 9

(Transalkylation)

| Component (wt %) | before reaction | after reaction |
|---|---|---|
| dimethylnaphthalene | 5.59 | 21.40 |
| 2,6-DMN | 0 | 2.24 |
| 2,7-DMN | 0 | 2.09 |
| other isomers | 5.59 | 17.07 |
| monomethylnaphthalene | 0 | 10.43 |
| 2-MMN | 0 | 7.28 |
| 1-MMN | 0 | 3.15 |
| naphthalene | 24.41 | 12.75 |
| heavy components | 69.16 | 54.18 |
| other component | 0.84 | 1.24 |
| evaluation | | |
| NL conversion (%) | — | 47.77 |
| heavies conversion (%) | — | 21.66 |

As can be seen from Table 9, heavy components can be converted into DMNs and MMNs in this transalkylation process

EXAMPLE 9

(Alkylation of Monomethylnaphthalene and Naphthalene)

A 153 g amount of MCM-22 is charged into a tubular reactor (volume: 370 cc). As a feedstock for alkylation, 1-MMN, 2-MMN and naphthalene are used, and mixed at a molar ratio of 2.2 of 2-MMN/1-MMN, and a weight ratio of 3.0 of MMNs (1-MMN+2-MMN)/naphthalene.

Thereupon, the feedstock is supplied to the reactor (254° C., 5 kg/cm$^2$) at a rate of 153.4 g/hr and 1.0 hr$^{-1}$ in WHSV with a feed of hydrogen at the rate of 1.8 ft$^3$/hr. Four hours later, methanol, as an alkylating agent, is introduced into the reactor at 35.5 g/hr, and alkylation is conducted for 20 hours. The product obtained is analyzed by gas chromatography, and the results are summarized in Table 10.

TABLE 10

(Alkylation of Monomethylnaphthalene and Naphthalene)

| Component (wt %) | before reaction | after reaction |
|---|---|---|
| dimethylnaphthalene | 0 | 17.19 |
| 2,6-DMN | 0 | 1.72 |
| 2,7-DMN | 0 | 1.20 |
| other isomers | 0 | 14.27 |
| monomethylnaphthalene | 73.63 | 60.10 |
| 2-MMN | 50.55 | 40.32 |
| 1-MMN | 23.08 | 19.78 |
| naphthalene | 25.28 | 18.67 |
| other component | 1.00 | |
| evaluation | | |
| NL conversion (%) | — | 26.15 |
| 2-MMN/1-MMN | 2.2 | 2.04 |
| MMN conversion (%) | — | 18.37 |
| 2,6-DMN/total DMN (%) | — | 10.02 |
| 2,6-DMN/2,7-DMN | — | 1.44 |

As can be seen from Table 10, the ratio of 2,6-DMN/2,7-DMN is over 1.1 and the ratio of 2-MMN/1-MMN is over 2.0.

Obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A process for producing 2,6-dialkylnaphthalene, comprising the steps:

(I) transalkylating isomers of dialkylnaphthalene and naphthalene to produce monoalkylnaphthalene and simultaneously isomerizing isomers of dialkylnaphthalene;

(II) separating the product obtained in step (I) into naphthalene, monoalkylnaphthalene, dialkylnaphthalene and other components;

(III) alkylating the monoalkylnaphthalene fraction of step (II) with an alkylating agent to produce dialkylnaphthalene; and (IV) separating 2,6-dialkylnaphthalene from the dialkylnaphthalene fraction in step (II), wherein step (I) and step (III) are conducted in the presence of a catalyst having a composition comprising a synthetic zeolite having an X-ray diffraction pattern with an interplanar d-spacing (Å)

```
12.36 ± 0.4
11.03 ± 0.2
8.83 ± 0.14
6.18 ± 0.12
6.00 ± 0.10
4.06 ± 0.07
3.91 ± 0.07
3.42 ± 0.06.
```

2. The process of claim 1, wherein the naphthalene fraction of step (II) is recycled to step (I) and/or step (III), the product of step (III) is recycled to step (II), and a dialkylnaphthalene fraction, after 2,6-dialkylnaphthalene is separated therefrom in step (IV), is recycled to step (I).

3. The process of claim 1, wherein a feedstock of step (I) comprises less than 11 weight % of 2,6-dialkylnaphthalene.

4. The process of claim 1, wherein the molar ratio of 2-monoalkylnaphthalene/1-monoalkylnaphthalene produced in step (I) is more than 2.0.

5. The process of claim 1, wherein the molar ratio of 2,6-dialkylnaphthalene/2,7 dialkylnaphthalene of the product in step (I) is more than 1.2.

6. The process of claim 1, wherein the molar ratio of 2,6-dialkylnaphthalene after isomerizing/2,6-dialkylnaphthalene before isomerizing in step (I) is more than 1.1.

7. The process of claim 1, wherein the molar ratio of 2,6-dialkylnaphthalene/2,7 dialkylnaphthalene of the product in step (III) is more than 1.1.

8. The process of claim 1, wherein the molar ratio of naphthalene/dialkylnaphthalene in a feedstock of step (I) is less than 1.0.

9. The process of claim 1, wherein naphthalene is fed to step (III).

10. The process of claim 9, wherein the molar ratio of naphthalene/monoalkylnaphthalene in a feedstock of step (III) is from about 1/3 to 3/1.

11. The process of claim 1, wherein (i) the dialkylnaphthalene fraction from step (II) is separated into 2,6-rich-dialkylnaphthalene and 2,6-lean-dialkylnaphthalene, (ii) the 2,6-rich dialkylnaphthalene is utilized in separating 2,6-dialkylnaphthalene in step (IV), and (iii) the 2,6-lean-dialkylnaphthalene is recycled to step (I).

12. The process of claim 11, wherein a part of the 2,6-lean-dialkylnaphthalene is isomerized in the presence of a catalyst composition comprising a synthetic zeolite having an X-ray diffraction pattern with an interplanar d-spacing (Å)

```
12.36 ± 0.4
11.03 ± 0.2
8.83 ± 0.14
6.18 ± 0.12
6.00 ± 0.10
4.06 ± 0.07
3.91 ± 0.07
3.42 ± 0.06,
``` and the product in the isomerization is recycled to step (II) and/or step (IV).

13. The process of claim 1, wherein a part of the dialkylnaphthalene fraction after 2,6-dialkylnaphthalene is separated therefrom in step (IV) is isomerized in the presence of a catalyst composition comprising a synthetic zeolite having an X-ray diffraction pattern with an interplanar d-spacing (Å)

```
12.36 ± 0.4
11.03 ± 0.2
8.83 ± 0.14
6.18 ± 0.12
6.00 ± 0.10
4.06 ± 0.07
3.91 ± 0.07
3.42 ± 0.06,
``` and the product in the isomerization is recycled to step (II) and/or step (IV).

14. The process of claim 1, wherein polyalkylnaphthalenes which have more than two alkyl groups are separated in step (II), and said polyalkylnaphthalenes are recycled to step (I).

15. The process of claim 1, wherein 2,6-dialkylnaphthalene is separated by crystallization under high pressure in step (IV).

16. The process of claim 1, wherein the dialkylnaphthalene is dimethylnaphthalene and the monoalkylnaphthalene is monomethylnaphthalene.

17. The process of claim 1, wherein the alkylating agent is methanol or dimethylether.

18. A process of preparing a polyethylenenaphthalate polymer or polybutylenenaphthalate polymer, comprising:
  A) oxidizing 2,6-dialkylnaphthalene to form 2,6-naphthalene-dicarboxylic acid; and
  B) condensing said 2,6-naphthalene-dicarboxylic acid with ethylene glycol or butanediol to form polyethylenenaphthalate or polybutylenenaphthalate;
wherein said 2,6-di-alkylnaphthalene is prepared by a process comprising the steps of:
  (I) transalkylating isomers of dialkylnaphthalene and naphthalene thereby producing monoalkylnaphthalene and simultaneously isomerizing isomers of dialkylnaphthalene,
  (II) separating the product from said step (I) into naphthalene, monoalkylnaphthalene, dialkylnaphthalene and other components;
  (III) alkylating the monoalkylnaphthalene fraction from step (II) with an alkylating agent to produce dialkylnaphthalenes, and
  (IV) separating 2,6-dialkylnaphthalene from the dialkylnaphthalene fraction in step (II),
wherein step (I) and step (III) are conducted in the presence of a catalyst composition comprising a synthetic zeolite having an X-ray diffraction pattern with an interplanar d-spacing (Å)

```
12.36 ± 0.4
11.03 ± 0.2
8.83 ± 0.14
6.18 ± 0.12
6.00 ± 0.10
4.06 ± 0.07
3.91 ± 0.07
3.42 ± 0.06.
```

19. A process of preparing a polyethylenenaphthalate polymer or polybutylenenaphthalate polymer, comprising;
  A) oxidizing 2,6-dialkylnaphthalene to form 2,6-naphthalene-dicarboxylic acid; and
  B) esterifying 2,6-naphthalene-dicarboxylic acid with methanol to form dimethyl 2,6-naphthalene-dicarboxylate; and C) condensing said dimethyl-2,6-naphthalene-dicarboxylate with ethylene glycol or butanediol to form a polyethylenenaphthalate polymer or polybutylenenaphthalate polymer, wherein said 2,6-dialkylnaphthalene is prepared by a process comprising the steps of:

(I) transalkylating isomers of dialkylnaphthalene and naphthalene to produce monoalkylnaphthalene and simultaneously isomerizing isomers of dialkylnaphthalene;

(II) separating the product from said step (I) into naphthalene, monoalkylnaphthalene, dialkylnaphthalene and other components;

(III) alkylating the monoalkylnaphthalene fraction from step (II) with an alkylating agent to produce dialkylnaphthalene;

(IV) separating 2,6-dialkylnaphthalene from the dialkylnaphthalene fraction in step (II), wherein step (I) and step (III) are conducted in the presence of a catalyst composition comprising a synthetic zeolite having an X-ray diffraction pattern with an interplanar d-spacing (Å)

| |
|---|
| $12.36 \pm 0.4$ |
| $11.03 \pm 0.2$ |
| $8.83 \pm 0.14$ |
| $6.18 \pm 0.12$ |
| $6.00 \pm 0.10$ |
| $4.06 \pm 0.07$ |
| $3.91 \pm 0.07$ |
| $3.42 \pm 0.06.$ |

* * * * *

UNITED STATES PATENT AND TRADEMARK OFFICE
CERTIFICATE OF CORRECTION

PATENT NO.   : 6,011,190
DATED        : January 4, 2000
INVENTOR(S)  : Masahiro Motoyuki et al Page 1 of 1

It is certified that error appears in the above-identified patent and that said Letters Patent is hereby corrected as shown below:

Column 2,
Line 25, please delete the formula in its entirety and insert therefor

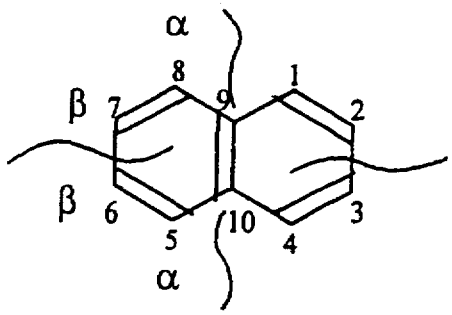

Column 10,
Line 65, "(1)Crystallization under High Pressure Crystallization" should read -- (1) Crystallization under High Pressure --.

Column 14,
Line 33, "other component    1.00" should read -- other component    1.00    3.91 --.

Signed and Sealed this

Twenty-fifth Day of December, 2001

Attest:

*Attesting Officer*

JAMES E. ROGAN
*Director of the United States Patent and Trademark Office*